United States Patent Office

Plant Pat. 2,961
Patented Jan. 20, 1970

2,961
GRAPEVINE

Louis A. Gebhart, Fresno, Calif., assignor to John J. Kovacevich, Arvin, Calif.

No Drawing. Filed Mar. 21, 1968, Ser. No. 725,548
Int. Cl. A01h 5/08
U.S. Cl. Plt.—47 1 Claim The present invention relates to a new and distinct variety of grapevine.

The new variety of grapevine originated in a vineyard of Thompson seedless grapevines (unpatented) maintained by the applicant's employer, John J. Kovacevich, on his ranch near Arvin, Calif. The climatic conditions existing in the subject vineyard are typical of those enjoyed by the San Joaquin Valley of central California and include a mild winter of light rainfall (approximately 10 inches) and a hot, dry summer. During the maintenance of said vineyard, the applicant recognized the new variety as a chance variation or mutation growing on a single Thompson seedles grapevine which it most nearly resembles. The Thompson variety grapevine is that unpatented variety known in the Middle East under the name "Sultania," in Australia and South Africa as "Sultana," in Greece as "Sultanine" and in Great Britain as "Lady Decoverly." When originally discovered, it was noted that the new variety bloomed approximately one week earlier than the Thompson. Furthermore, the fruit of the new variety ripened approximately from seven to ten days earlier than the Thompson while retaining the latter's desirable seedless characteristics and production of relatively large densely populated clusters of berries. It was further noted that the berries of the new variety ripened more uniformly than the later maturing Thompson grape thoughout even the most densely populated clusters.

After having discovered the new variety as a chance variation of the Thompson, the grapevine of the present invention was asexually reproduced by four cuttings from the parent plant on the applicant's property at 4633 E. Liberty Ave. in Fresno, Calif. Two years later, eighty vines were grafted by the applicant to the new variety at the above designated Kovacevich vineyard near Arvin, Calif. The fruit subsequently borne by vines from the cuttings and grafts had the same distinctive early blooming and maturing characteristics observed in the fruit of the originally discovered chance variation. The uniform ripening of the berries throughout the relatively large, densely populated clusters is typical of the fruit borne by the vines of the subject variety.

The grapevine of the subject variety is, in all significant respects, identical in appearance to the Thompson variety. Since no visual distinctions are susceptible of illustration by drawing, no drawing is provided.

The following is a detailed description of the pomological characteristics of the subject grapevine. Where dimensions, sizes, colors and other characteristics are given, it is to be understood that such characteristics are approximations of averages set forth as accurately as practical.

Vine: Substantially identical in characteristics to that of the Thompson.

*Size.*—Large—but seldom attaining the trunk size of the Emperor (unpatented) grapevine.

*Growth.*—Vigorous.

*Productivity.*—Heavy and regular.

*Canes.*—Medium to stout. Joints—longer than usual. Tendrils—slender to medium and medium in length, number and strength. Color—light green during growth, turning to brown in the fall.

Foliage:

*Leaves.*—Number—average; similar to Thompson. Color—light greenish-yellow, becoming yellowish to brown in late fall.

Flowers:

*Number.*—Abundant.

*Bloom.*—Beginning approximately mid-April, about one week earlier than the Thompson.

*Blossom color.*—Inconspicuous—yellowish due to open anthers and abundant pollen.

*Shape and size of cluster.*—Conical and usually heavily shouldered.

*Average length of peduncle.*—4 inches.

Fruit:

*Maturity.*—Approximate dates—from about July 15 for fresh eating and August 10 for drying and wine production.

*Size of berry.*—Similar to Thompson and susceptible to artificial stimulation by girdling, hormone treatments, and the like.

*Diameter.*—From ⅜ of an inch to ½ of an inch under normal growing conditions without girdling or hormone treatment.

*Base to apex.*—From ⅝ of an inch to ¾ of an inch without girdling or hormone treatment.

*Average number of clusters to a vine.*—Thirty.

*Average number of berries to a cluster.*—Four-hundred.

*Number of seeds to berry.*—None.

*Productivity.*—Heavy.

*Skin.*—Tight—medium tough.

*Color.*—Skin of uniformly over-all light golden yellow.

*Ripening.*—One week to ten days ahead of Thompson variety. First week of July in Arvin area for fresh eating. Slightly later for wine and raisins.

*Clusters ripen.*—Evenly.

*Texture.*—Medium.

*Flavor.*—Sprightly sweet.

*Aroma.*—Delicate.

*Eating quality.*—Excellent.

*Juice quality.*—Excellent.

*Shipping quality.*—Excellent.

*Uses.*—Fresh table, raisins and wine.

The new variety grapevine has been described as it exists under the ecological conditions prevailing in the central San Joaquin Valley of California. Normal variations can be expected under different environmental conditions.

Having thus described the instant grapevine, I claim:

1. A new and distinct variety of grapevine substantially as described, characterized principally by its seedless berries growing in densely populated clusters similar to the Thompson variety grapevine, which it most nearly resembles, but from which it is distinguished by its earlier blooming and the ripening of its berries approximately seven to ten days earlier with said berries ripening more uniformly throughout said densely populated clusters than do the berries of the Thompson variety.

No references cited.

ROBERT E. BAGWILL, Primary Examiner